US012115358B2

(12) United States Patent
Jensen et al.

(10) Patent No.: US 12,115,358 B2
(45) Date of Patent: Oct. 15, 2024

(54) DRUG DELIVERY DEVICE WITH DOSE COUNTING MECHANISM

(71) Applicant: Novo Nordisk A/S, Bagsvaerd (DK)

(72) Inventors: Nicolai Michael Jensen, Koebenhaven SV (DK); Klaus Bendix, Vanloese (DK)

(73) Assignee: Novo Nordisk A/S, Bagsvaerd (DK)

( * ) Notice: Subject to any disclaimer, the term of this patent is extended or adjusted under 35 U.S.C. 154(b) by 1048 days.

(21) Appl. No.: 16/981,328

(22) PCT Filed: Mar. 22, 2019

(86) PCT No.: PCT/EP2019/057261
§ 371 (c)(1),
(2) Date: Sep. 16, 2020

(87) PCT Pub. No.: WO2019/180214
PCT Pub. Date: Sep. 26, 2019

(65) Prior Publication Data
US 2021/0023310 A1    Jan. 28, 2021

(30) Foreign Application Priority Data
Mar. 23, 2018   (EP) ..................................... 18163689

(51) Int. Cl.
*A61M 5/315*      (2006.01)
*A61M 5/20*       (2006.01)
(Continued)

(52) U.S. Cl.
CPC ...... *A61M 5/31595* (2013.01); *A61M 5/2033* (2013.01); *A61M 5/31526* (2013.01); *A61M 5/3202* (2013.01); *A61M 2005/3126* (2013.01)

(58) Field of Classification Search
CPC ............ A61M 5/31595; A61M 5/2033; A61M 5/31526; A61M 5/3202; A61M 5/31568; A61M 5/31583
See application file for complete search history.

(56) References Cited

U.S. PATENT DOCUMENTS 5,092,842 A * 3/1992 Bechtold .................. A61M 5/20
604/209
6,899,699 B2 * 5/2005 Enggaard .......... A61M 5/31553
604/207
(Continued)

FOREIGN PATENT DOCUMENTS

EP          2633874 A1     9/2013
JP       2005514120 A      5/2005
(Continued)

*Primary Examiner* — Jason E Flick
*Assistant Examiner* — Adam J. Cermak
(74) *Attorney, Agent, or Firm* — Wesley Nicolas

(57) ABSTRACT

A drug delivery device includes a dose counting mechanism and an end-of-content or remaining-dose indication. For example, a dose expelling mechanism is coupled to a reciprocating element configured to undergo a predefined motion during each dose expelling action to allow a dose to be expelled. The predefined motion includes displacement in a first axial direction from a first position to a second position followed by displacement in a second axial direction from the second position to the first position, with a counter element being movable in the first axial direction. First and second unidirectional ratchet mechanisms prevent motion in the first axial direction and allow motion in the second axial direction of the reciprocating element relative to the counter element, and vice versa, respectively.

8 Claims, 8 Drawing Sheets

(51) Int. Cl.
*A61M 5/31* (2006.01)
*A61M 5/32* (2006.01)

(56) References Cited

U.S. PATENT DOCUMENTS

| | | | |
|---|---|---|---|
| 10,441,725 B2 * | 10/2019 | Jones | A61M 5/31591 |
| 10,596,328 B2 * | 3/2020 | Plambech | A61M 5/2033 |
| 10,688,246 B2 * | 6/2020 | Morris | A61M 5/31575 |
| 2005/0090782 A1 * | 4/2005 | Marshall | A61M 5/31555 |
| | | | 604/211 |
| 2015/0174335 A1 * | 6/2015 | Roervig | A61M 5/347 |
| | | | 604/198 |
| 2016/0022919 A1 * | 1/2016 | Cammish | A61M 5/31575 |
| | | | 604/209 |
| 2016/0045669 A1 * | 2/2016 | Bayer | A61M 5/31541 |
| | | | 604/207 |
| 2016/0129188 A1 * | 5/2016 | Kiilerich | A61M 5/31555 |
| | | | 604/228 |
| 2016/0220759 A1 * | 8/2016 | Enggaard | A61M 5/3202 |
| 2016/0317751 A1 * | 11/2016 | Andersen | A61M 5/20 |
| 2017/0259006 A1 * | 9/2017 | Avery | A61M 5/20 |
| 2017/0296753 A1 * | 10/2017 | Rowe | A61M 5/31515 |
| 2017/0340836 A1 * | 11/2017 | Kiilerich | A61M 5/20 |
| 2020/0164153 A1 * | 5/2020 | Smith | A61M 5/31526 |
| 2020/0188594 A1 * | 6/2020 | Carrel | A61M 5/20 |
| 2021/0023310 A1 * | 1/2021 | Jensen | A61M 5/31526 |

FOREIGN PATENT DOCUMENTS

| | | | | |
|---|---|---|---|---|
| WO | 0119434 A1 | 3/2001 | | |
| WO | 2014001319 A1 | 1/2014 | | |
| WO | WO-2016102526 A1 * | 6/2016 | | A61M 5/20 |
| WO | 2016201586 A1 | 12/2016 | | |

* cited by examiner (a)

(b)

(a)

(b)

DRUG DELIVERY DEVICE WITH DOSE COUNTING MECHANISM

CROSS-REFERENCE TO RELATED APPLICATIONS

This application is a 35 U.S.C. § 371 National Stage application of International Application PCT/EP2019/057261 (published as WO/2019/180214), filed Mar. 22, 2019, which claims priority to European Patent Application 18163689.5, filed Mar. 23, 2018, the contents of all above-named applications are incorporated herein by reference.

FIELD OF THE INVENTION

The present invention relates generally to drug delivery devices and more specifically to fixed dose delivery devices having remaining dose indication means.

BACKGROUND OF THE INVENTION

For people self-administering drugs it has been customary to use kits comprising a drug filled vial, a syringe with a needle, and an alcohol swab. Within some disease areas and in some countries such kits are increasingly being replaced by pen injection devices. Pen injection devices are particularly convenient in that they allow the user to perform a dosed injection from a prefilled drug reservoir without first having to manually transfer the particular dose from one reservoir (the vial) to another (the syringe).

Predominantly, two types of pen injection devices are available, durable injection devices being capable of delivering one or more doses of drug from a prefilled drug cartridge which can be loaded into the device before use and replaced after exhaustion, and disposable injection devices being capable of delivering one or more doses of drug from a prefilled and non-exchangeable drug cartridge. Each of these types of pen injection devices are, or may in principle be, realised in various sub-types, such as e.g. single shot devices adapted to deliver only one dose from a drug cartridge, multi-shot devices capable of delivering a plurality of doses from a drug cartridge, manual devices, where the user provides the force needed for injection, automatic devices having a built-in energy source releasable to occasion the injection, fixed dose devices adapted to deliver a predetermined dose of drug, variable dose devices offering delivery of different doses of drug, settable by the user, etc.

As the labels suggest a durable injection device is intended for use over a considerable period of time during which multiple drug cartridges are exhausted and replaced, whereas a disposable injection device is intended for use until its dedicated drug cartridge is exhausted, after which the entire injection device is discarded.

Multi-shot devices can be of the fixed dose type or the variable dose type, and the drug expelling mechanisms in such devices can be mechanical, i.e. where movements of the piston rod are controlled mechanically, such as in manual devices or spring-driven devices, or electro-mechanical, i.e. where movements of the piston rod are controlled electronically, such as in electro-motor driven devices.

Multi-shot devices should ideally be provided with an end-of-content indication to prevent the potentially dangerous situation where a user performs a dose expelling action but does not receive the entire expected dose because the expected dose exceeds the dose remaining in the drug reservoir. Such end-of-content indication tends to add to the complexity and cost of the device construction.

WO 01/19434 (Novo Nordisk A/S) discloses examples of such end-of-content indication mechanisms for use in different types of injection devices, where the end-of-content indication is obtained by relative rotational motion between components of the respective devices. However, these solutions are not attractive to all types of multi-shot devices.

SUMMARY OF THE INVENTION

It is an object of the invention to eliminate or reduce at least one drawback of the prior art, or to provide a useful alternative to prior art solutions.

In particular, it is an object of the invention to provide a multi-shot drug delivery device having a simple and cost-efficient end-of-content indication means.

It is a further object of the invention to provide a simple and reliable counting mechanism for keeping track of the number of doses expelled by a fixed dose type of multi-shot delivery device and/or of the number of doses still available for injection.

In the disclosure of the present invention, aspects and embodiments will be described which will address one or more of the above objects and/or which will address objects apparent from the following text.

A drug delivery device embodying the principles of the invention is configured to execute a predetermined number of dose expelling actions and comprises a housing accommodating a dose expelling mechanism, activation means configured to undergo a predefined motion relative to the housing during each dose expelling action to allow a dose to be expelled, the predefined motion comprising displacement from a first position to a second position and back to the first position, and counting means operatively coupled with the activation means and configured to change state responsive to the activation means undergoing the predefined motion.

A simple way of keeping track of the number of doses expelled by the drug delivery device is thereby provided, as the counting means changes state when, and only when, the activation means is displaced in connection with a dose expelling action. If, for example, the counting means comprises an electronic transducer, this transducer may be operatively coupled with an electronic display which is configured to visually represent a use related state of the drug delivery device, such as an accumulated number of dose expelling actions performed.

In a mechanical version, the counting means may for example be configured to move in a forward counting direction relative to the housing in response to a displacement of the activation means from the first position to the second position and to remain stationary in response to a displacement of the activation means from the second position to the first position. Such movement pattern may be realised by a first unidirectional ratchet mechanism acting between the activation means and the counting means, in combination with a second unidirectional ratchet mechanism acting between the counting means and the housing, or a component fixed with respect to the housing, where the first unidirectional ratchet mechanism prevents motion of the activation means relative to the counting means in the forward counting direction, and the second unidirectional ratchet mechanism prevents motion of the counting means relative to the housing in a direction opposite to the forward counting direction.

The drug delivery device may further comprise end-of-content indication means being operatively coupled with the counting means and the activation means and configured to become activated responsive to the counting means having changed state a plurality of times corresponding to the predetermined number of dose expelling actions.

The activation of the end-of-content indication means provides a signal to the user that the predetermined number of dose expelling actions have been performed, indicating that the drug delivery device should be discarded. The signal may be electronic, such as e.g. an indication on an electronic display, or mechanical.

The end-of-content indication means may comprise lock-out means being operatively coupled with the counting means and the activation means and configured to prevent displacement of the activation means from the first position to the second position responsive to the counting means having changed state a plurality of times corresponding to the predetermined number of dose expelling actions.

Since the displacement of the activation means from the first position to the second position is a prerequisite for initiation of a dose expelling action no dose expelling action can be initiated once the counting means has changed state said plurality of times and the lockout means are in effect. It is thus ensured that any attempt to execute a further dose expelling action with the drug delivery device after the predetermined number of dose expelling actions has been performed will be unsuccessful.

The drug delivery device may e.g. be electronically monitored, controlled or driven, or it may be a purely mechanical device devoid of any electronic components.

In one aspect of the invention a drug delivery device according to claim 1 is provided.

Accordingly, a drug delivery device for executing a predetermined number of dose expelling actions is provided. The drug delivery device, which may e.g. be a drug injection device, a drug infusion device, a drug inhalation device, or the like, comprises a housing extending along an axis and accommodating a dose expelling mechanism, and activation means in the form of a reciprocating element being operatively coupled with the dose expelling mechanism and configured to undergo a predefined motion relative to the housing during each dose expelling action to allow a dose to be expelled. The predefined motion comprises displacement in a first axial direction from a first position to a second position followed by displacement in a second axial direction, opposite to the first axial direction, from the second position to the first position. The drug delivery device further comprises counting means in the form of a counter element being movable in the first axial direction relative to the housing, a first unidirectional ratchet mechanism preventing motion in the first axial direction while allowing motion in the second axial direction of the reciprocating element relative to the counter element, and a second unidirectional ratchet mechanism allowing motion in the first axial direction while preventing motion in the second axial direction of the counter element relative to the housing.

Hence, at each dose expelling action the counter element is forced in the first axial direction by the reciprocating element during the displacement of the reciprocating element from the first position to the second position and passed partly by the reciprocating element during the following displacement of the reciprocating element from the second position back to the first position. Thereby, the counter element crawls incrementally along the first axial direction as dose expelling actions are executed, i.e. at each dose expelling action the counter element undergoes an incremental displacement relative to the housing, and the number of such incremental displacements corresponds to the number of dose expelling actions.

The position of the counter element relative to the housing is thus indicative of the number of dose expelling actions currently executed by the drug delivery device, and the number of dose expelling actions available is accordingly derivable as the predetermined number of dose expelling actions minus the number of dose expelling actions currently executed. In case the drug delivery device further comprises electronics for monitoring one or more activities on or by the drug delivery device such electronics may comprise means for registering a dose expelling action and for keeping count of the number of dose expelling actions currently executed as well as potentially the number of dose expelling actions available. The electronics may further comprise a display for presentation of at least some of this information. In case the drug delivery device is a purely mechanical device the housing may comprise a window allowing for visual inspection of the position of the counter element. A graduation scale may additionally be arranged to provide for a reading of e.g. the number of incremental displacements of the counter element.

The drug delivery device may further comprise a base member being axially and rotationally fixed with respect to the housing. The first unidirectional ratchet mechanism may comprise a first axial toothing on one of the reciprocating element and the counter element and a pawl member on the other of the reciprocating element and the counter element, and the second unidirectional ratchet mechanism may comprise a second axial toothing on one of the counter element and the base member and a pawl member on the other of the counter element and the base member.

The counter element may be configured to undergo motion in the first axial direction relative to the housing from a pre-use position assumed prior to the first dose expelling action to an end-of-content position in a number of steps which correspond to the predetermined number of dose expelling actions. At reaching the end-of-content position the counter element may enter into axial interlocking engagement with the base member and become prevented from further motion in the first axial direction relative to the housing. This will mechanically block further movements of the reciprocating element from the first position to the second position and thereby prevent initiation of further dose expelling actions, signaling to the user that a new drug delivery device is required.

The drug delivery device may further comprise a drug reservoir holder arranged in axial extension of the housing, and the dose expelling mechanism may comprise an activation structure being operable from a distal end portion of the drug reservoir holder to displace the reciprocating element in the first axial direction against a biasing force. It will thereby be possible to activate the dose expelling mechanism from the distal end of the drug delivery device.

The drug reservoir holder may comprise reception means for receiving a needle module at the distal end portion and provide for an operative coupling of an axially movable portion of the needle module with the activation structure. The needle module may comprise a needle base housing a needle hub which carries a skin-insertable front needle and has means for establishing fluid connection to one or more drug reservoirs. The needle base may be adapted for attachment to the drug reservoir holder in axial extension thereof, and the axially movable portion of the needle module may comprise a needle shield being axially movable relative to the needle base between a first shield position in which the front needle is covered and a second shield position in which the front needle is exposed to the surroundings.

The needle shield may be configured to displace the reciprocating element in the first axial direction in response to an uncovering of the skin insertable front needle, i.e. when moving from the first shield position to the second shield position. This provides for a needle shield triggered dose expelling mechanism and thereby a simple use pattern where the user need only place the needle shield against the skin and press the drug delivery device towards the skin to execute a dose expelling action.

The drug delivery device may further comprise a dose preparing structure configured to prepare a dose to be delivered from the drug delivery device in response to distal motion of a loading member relative to the housing, and a protective cap for the drug reservoir holder, the protective cap being operatively coupled with the dose preparing structure when covering the drug reservoir holder and configured to move the loading member distally relative to the housing in response to being dismounted from the cartridge holder. An automatic dose preparation action is thereby incorporated for the drug delivery device, whereby the mere dismounting of the protective cap from the drug reservoir holder readies the drug delivery device for expelling of a dose of drug. No further preparation steps are needed from the user in order to be able to execute a dose expelling action.

The dose expelling mechanism may be powered by a torsion spring member, and the dose preparing structure may comprise a spring straining mechanism for straining the torsion spring member. Accordingly, the dose preparing structure may be configured to convert distal motion of the loading member relative to the housing to rotation of a spring straining member relative to the housing. The spring straining mechanism may comprise a retention structure for retaining the torsion spring member in a strained state where it stores sufficient energy to cause a dose to be expelled from the drug delivery device upon activation of the dose expelling mechanism.

The counter element may be configured to enter into rotational interlocking engagement with the spring straining member in response to reaching the end-of-content position. Thereby, distal motion of the loading member relative to the housing will be prevented because the spring straining member is prevented from rotating relative to the housing. Consequently, depending on a particular engagement interface between the protective cap and the loading member, the protective cap will either be stuck on the drug reservoir holder, or much more difficult to dismount therefrom, providing a clear signal to the user that no further doses are available from the drug delivery device.

As used herein, the terms "distal" and "proximal" denote positions at or directions along a drug delivery device, where "distal" refers to the drug outlet end and "proximal" refers to the end opposite the drug outlet end.

In the present specification, reference to a certain aspect or a certain embodiment (e.g. "an aspect", "a first aspect", "one embodiment", "an exemplary embodiment", or the like) signifies that a particular feature, structure, or characteristic described in connection with the respective aspect or embodiment is included in, or inherent of, at least that one aspect or embodiment of the invention, but not necessarily in/of all aspects or embodiments of the invention. It is emphasized, however, that any combination of the various features, structures and/or characteristics described in relation to the invention is encompassed by the invention unless expressly stated herein or clearly contradicted by context.

The use of any and all examples, or exemplary language (e.g., such as, etc.), in the text is intended to merely illuminate the invention and does not pose a limitation on the scope of the same, unless otherwise claimed. Further, no language or wording in the specification should be construed as indicating any non-claimed element as essential to the practice of the invention.

BRIEF DESCRIPTION OF THE DRAWINGS

In the following the invention will be further described with references to the drawings, wherein.

DESCRIPTION OF EXEMPLARY EMBODIMENTS

Figure 1:
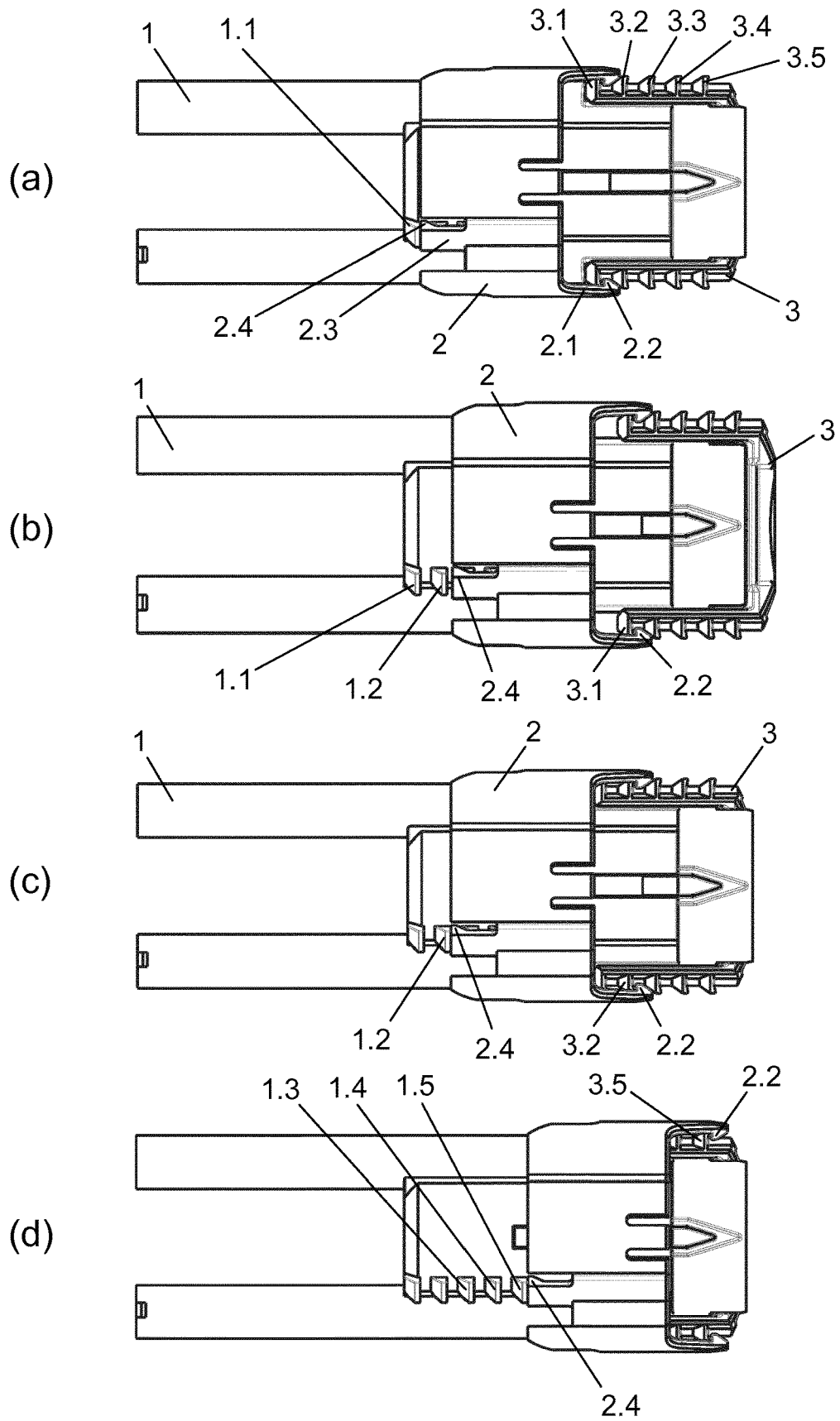
FIGS. 1(a)-(d) illustrates the working principle of a dose counting mechanism according to an exemplary embodiment of the invention.

When in the following relative expressions, such as "upwards" and "downwards" and "left" and "right", are used, these refer to the appended figures and not necessarily to an actual situation of use. The shown figures are schematic representations for which reason the configuration of the different structures as well as their relative dimensions are intended to serve illustrative purposes only.

FIG. 1a-d illustrate the principle of a dose counting mechanism for a drug delivery device according to an embodiment of the invention through side views of three interacting components in different states from start to end of a use period.

A first component 1 extends along a longitudinal axis and comprises a first array of teeth which extends axially from a distal tooth 1.1 to a proximal tooth 1.5. This particular array of teeth has a second tooth 1.2, a third tooth 1.3, and a fourth tooth 1.4 arranged between the distal tooth 1.1 and the proximal tooth 1.5, i.e. it consists of a total of five teeth.

A second component 2 is arranged exteriorly of the first component 1 and comprises a pair of radially opposite arms 2.1, each arm 2.1 being radially deflectable, extending towards the right and ending in a hook 2.2. The second component 2 further comprises a radially deflectable leg 2.3 extending towards the left. The leg 2.3 ends in a foot 2.4 which in FIG. 1a rests on the distal tooth 1.1. This constitutes the initial state of the dose counting mechanism. In the context of a drug delivery device, since the distal tooth 1.1 is dedicated to initially hold the second component 2 the number of remaining teeth in the first array of teeth to which the foot 2.4 may be moved is four, and the total number of doses offered to the user is thus four. This will be explained in further detail below.

The five teeth in the first array of teeth are uniformly shaped, each with a straight transversal right flank and a sloped left flank, and the foot 2.4 has a corresponding straight transversal left flank and a sloped right flank. Thereby, the first array of teeth and the leg 2.3 together constitute a first unidirectional ratchet mechanism, which allows movement to the right of the second component 2 relative to the first component 1 but restricts movement to the left of the second component 2 relative to the first component 1.

A third component 3 is arranged exteriorly of the first component 1 and comprises two parallel second arrays of teeth, each extending axially from a distal tooth 3.1 to a proximal tooth 3.5. For each second array of teeth a second tooth 3.2, a third tooth 3.3, and a fourth tooth 3.4 are arranged between the distal tooth 3.1 and the proximal tooth 3.5, similarly to the first array of teeth on the first component 1. The two hooks 2.2 are adapted for synchronous interaction with the two second arrays of teeth. However, in the following only the interaction between one of the hooks 2.2 and one of the second arrays of teeth will be described.

The five teeth in the second array of teeth are uniformly shaped, each with a straight transversal right flank and a sloped left flank, and the hook 2.2 has a corresponding straight transversal left flank and a sloped right flank. Thereby, the second array of teeth and the arm 2.1 together constitute a second unidirectional ratchet mechanism, which allows movement to the left of the third component 3 relative to the second component 2 but restricts movement to the right of the third component 3 relative to the second component 2.

In the initial state of the dose counting mechanism, as shown in FIG. 1a, the hook 2.2 engages with the distal tooth 3.1. The third component 3 is configured to perform reciprocating motion relative to the first component 1. In the course of one dose delivery action the third component 3 moves back and forth once. This means that every time a dose of drug has been expelled the third component 3 has moved relative to the first component 1 from a starting position to an intermediate position and back to the starting position. FIGS. 1a-c illustrate the relative movements involved during such dose expelling, where the third component 3 in FIG. 1b has moved right from the starting position to the intermediate position and in FIG. 1c has moved left from the intermediate position back to the starting position.

During the movement of the third component 3 from the starting position to the intermediate position the distal tooth 3.1 of the second array of teeth applies a force to the hook 2.2 and consequently forces the second component 2 to the right. Thereby, the foot 2.4 slides along the sloped left flank of, and passes, the second tooth 1.2 of the first array of teeth. During the subsequent movement of the third component 3 from the intermediate position back to the starting position the foot 2.4 rests against the transversal right flank of the second tooth 1.2 of the first array of teeth, preventing movement to the left of the second component 2 relative to the first component 1, which causes the second tooth 3.2 of the second array of teeth to slide along the sloped right flank of, and pass, the hook 2.2.

Following the first dose expelling action the second component 2 has thus been displaced incrementally along the first component 1 a distance corresponding to the distance between the transversal right flank of the distal tooth 1.1 of the first array of teeth and the transversal right flank of the second tooth 1.2 of the first array of teeth. Notably, the second component 2 has been displaced incrementally the same distance along the third component 3.

With the foot 2.4 now resting on the second tooth 1.2 of the first array of teeth and the hook 2.2 engaging the second tooth 3.2 of the second array of teeth (FIG. 1c) a next dose delivery action will cause the foot 2.4 to pass the third tooth 1.3 of the first array of teeth and the hook 2.2 to pass the third tooth 3.3 of the second array of teeth in a manner similar to the above described.

Following the second dose expelling action the foot 2.4 thus rests on the transversal right flank of the third tooth 1.3 of the first array of teeth and the hook 2.2 engages the transversal right flank of the third tooth 3.3 of the second array of teeth. This movement pattern continues until the last dose has been expelled, at which point the foot 2.4 rests on the transversal right flank of the proximal tooth 1.5 of the first array of teeth, and the hook 2.2 engages the transversal right flank of the proximal tooth 3.5 of the second array of teeth. In the present example this corresponds to four doses being expellable from the drug delivery device.

Figure 2:
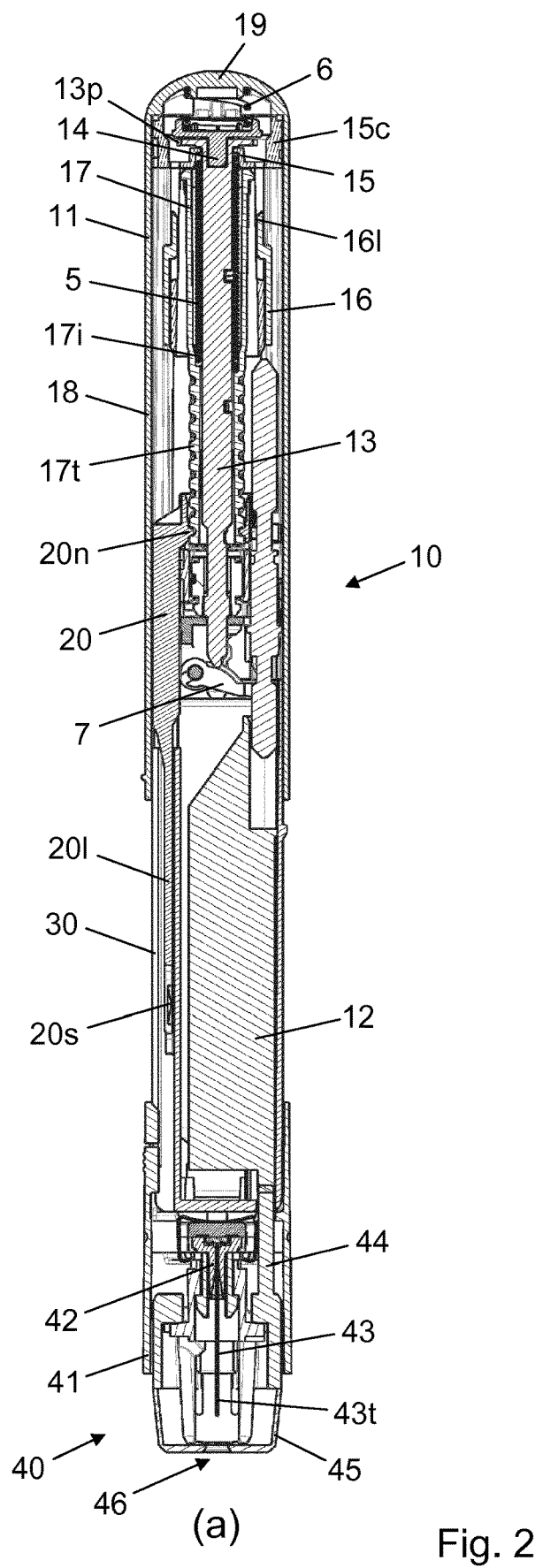
FIGS. 2(a)-(b) shows a longitudinal section view of an exemplary drug delivery device, employing the dose counting mechanism, in two different states.
Figure 2:
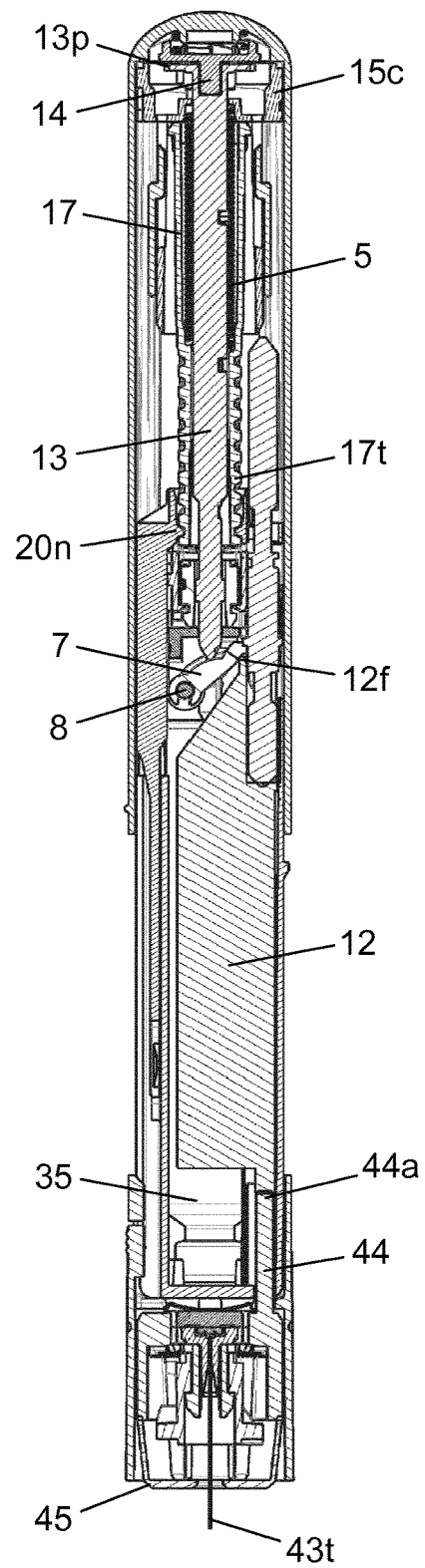

FIG. 2a is a longitudinal section view of a fixed dose injection device 10 employing a dose counting mechanism of the type described above. The injection device 10 comprises a housing 11 extending along a longitudinal axis and a cartridge holder 30 in axial extension thereof. The cartridge holder 30 accommodates a first cartridge 35 (ref. FIG. 2b) which holds a first substance and a second cartridge (not visible) which holds a second substance.

A needle module 40 is attached at the distal end of the cartridge holder 30. It comprises a needle base 41, which engages with a collar portion of the cartridge holder 30, and a needle hub 42, which holds a front needle 43 and two back needles (not visible). The front needle 43 is fluidly connected with each of the back needles, in a manifold configuration, and each back needle has fluid access to one of the two cartridges in the cartridge holder 30. The injection device 10 is thus capable of delivering two substances to one single delivery site.

The needle module 40 further comprises a needle shield 45 being axially movable relative to the needle base 41 and having a distal opening 46 for passage of a tip portion 43t of the front needle 43. An activator arm 44, which is axially fixed with respect to the needle shield 45, extends into the cartridge holder 30 and is in FIG. 2a prepared for interaction with an axially movable front activator 12. In the initial state of the needle module 40 on the injection device 10 the front needle 43 is safely accommodated within the needle shield 45.

The housing 11, which has a longitudinal side wall 18 of oval cross-section and is closed proximally by an end wall 19, accommodates a dose setting mechanism and an injection mechanism which will be described in the following. Each of the two cartridges comprises a cartridge wall, a distal penetrable self-sealing septum, and a proximal piston which is slidable along the cartridge wall by distal advancing motion of a piston rod (first piston rod 53, respectively second piston rod 54, ref. FIG. 3a) relative to the housing 11. Motion of the piston rods 53, 54 is powered by a drive spring 5 which is a torsion spring having a proximal spring end rotationally fixed to a spring base 15 and a distal spring end rotationally fixed to a spring clutch 17 at a spring interface 17i. The spring base 15 is fixed to the housing 11 via a spring base collar 15c.

Figure 8:
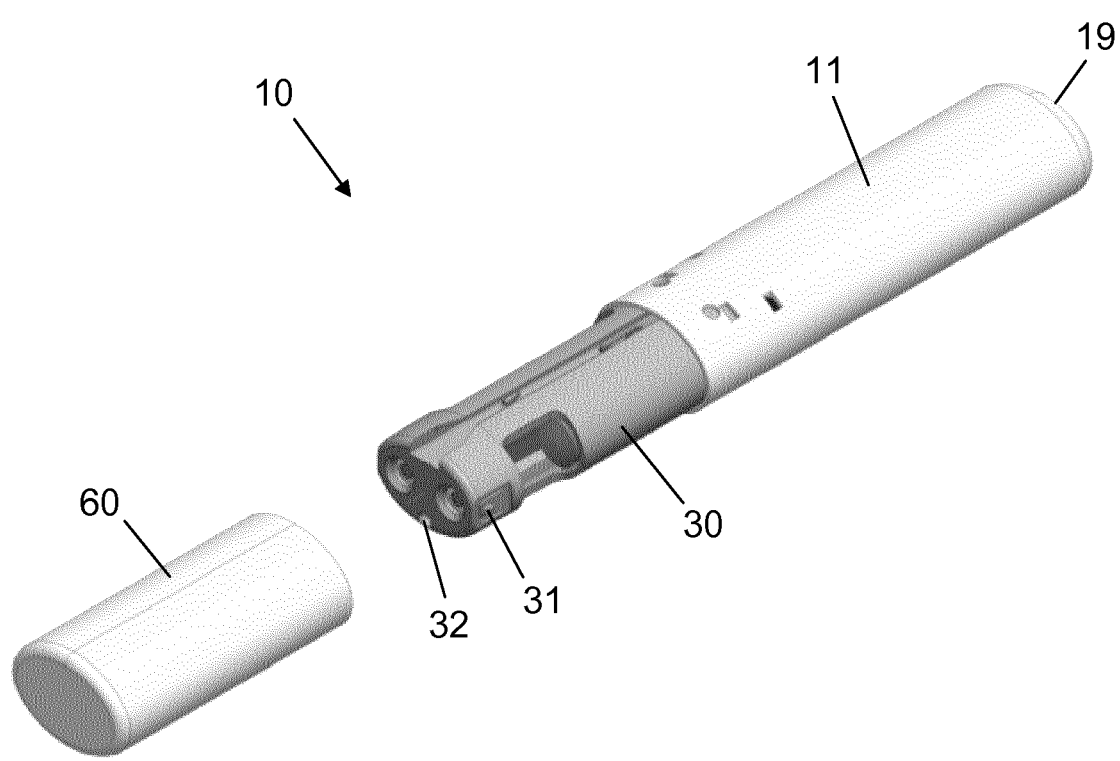

The spring clutch 17 is a hollow structure which is arranged rotatably with respect to the housing 11 and is provided with a non-self-locking thread 17t on a distal outer surface. The non-self-locking thread 17t extends axially approximately half the total length of the spring clutch 17 from a distal thread end to a proximal thread end and is configured for interaction with a loader nut 20n, forming part of a loader 20. The loader 20 further comprises an elongated loader leg 20*l* having a snap interface 20*s* to a protective cap 60 (ref. FIG. 8) for the cartridge holder 30. The loader 20 is axially movable, but prevented from rotation, relative to the housing 11, and the thread connection between the loader nut 20*n* and the non-self-locking thread 17*t* thus ensures that an axial motion of the loader 20 causes a rotation of the spring clutch 17, and vice versa.

The protective cap 60 is configured to engage with the snap interface 20*s* of the loader leg 20*l* and to pull the loader 20 axially in the distal direction when being dismounted from the cartridge holder 30. Such a cap dismounting action accordingly causes the spring clutch 17 to rotate and thereby the drive spring 5 to become angularly distorted. When the loader nut 20*n*, during the axial movement of the loader 20, reaches the distal thread end of the non-self-locking thread 17*t* a geometry (not visible) in the cartridge holder 30 allows for radially inwards flexing of the loader leg 20*l*, leading to disengagement of the protective cap 60.

A rear activator 13 extends longitudinally through the spring clutch 17, and whereas the spring clutch 17 is axially fixed with respect to the housing 11 the rear activator 13 is adapted for axial reciprocating motion during use of the injection device 10. The rear activator 13 has a distal end which contacts a tilting arm 7 and a proximal end which interfaces with a return member 14. The return member 14 is biased in the distal direction by a return spring 6. At the proximal end the rear activator 13 is provided with a diametrically opposite pair of pawls 13*p*, each pawl 13*p* being configured for interaction with the spring base collar 15*c* in a ratchet interface which restricts counter-clockwise rotation (seen from the proximal end) of the rear activator 13 relative to the housing 11. The rear activator 13 and the spring clutch 17 are rotationally interlocked via interacting splines on an exterior surface portion of the rear activator 13, respectively an interior surface portion of the spring clutch 17.

An end-of-content ring 16 is arranged exteriorly of, and configured for step-wise axial movement along, the spring base 15, as explained further below. The end-of-content ring 16 comprises a pair of diametrically opposite axially extending lock arms 16*l*, the purpose of which will be apparent from the following text.

In FIG. 2*a* the loader nut 20*n* is positioned at the distal thread end of the non-self-locking thread 17*t*, which corresponds to the above described situation where the protective cap 60 during axial dismounting from the cartridge holder 30 has pulled the loader 20 axially relative to the housing 11, whereby the spring clutch 17 has been rotated to strain the drive spring 5. The spring clutch 17, being rotationally locked to the rear activator 13, is locked in this angular position by the ratchet engagement between the spring base collar 15*c* and the pawls 13*p*. Rotational energy is thus stored in the drive spring 5, and the injection device is ready to deliver respective predetermined doses of the substances in the two cartridges. Hence, in practice a dose setting action is performed by dismounting the protective cap 60 from the cartridge holder 30. In alternative embodiments of the invention, the protective cap 60 is not configured for engagement with the loader 20, and the user manually strains the drive spring 5 by pulling the loader leg 20*l* in a separate action.

FIG. 2*b* shows the injection device 10 in a state where the needle shield 45 is placed against the skin of a user and the housing 11 is pressed towards the skin, such that the needle shield 45 is moved proximally relative to the needle base 41, causing the tip portion 43*t* to protrude through the opening 46. The movement of the needle shield 45 further causes an abutment portion 44*a* of the activator arm 44 to push the front activator 12 proximally relative to the cartridge holder 30, whereby a proximal finger 12*f* of the front activator 12 activates the tilting arm 7 which pivots about the fulcrum 8 and causes a proximal displacement of the rear activator 13 that equals ⅓ the proximal displacement of the front activator 12.

By the proximal movement of the rear activator 13, the return member 14 is pressed towards the end wall 19 against the bias of the return spring 6, and the pawls 13*p* are lifted out of the engagement with the spring base collar 15*c*, thereby releasing the strained drive spring 5. Since the proximal spring end is fixed with respect to the housing 11 the release of the stored rotational energy causes the distal spring end, and thereby the spring clutch 17 and the rear activator 13, to rotate about the longitudinal axis. As will be explained below this rotation causes the predetermined doses of the two substances to be delivered from the injection device 10.

When the user subsequently withdraws the tip portion 43*t* from the skin the return spring 6 returns the entire system comprising the return member 14, the rear activator 13, the front activator 12, via the tilting arm 7, the activator arm 44, and the needle shield 45 distally relative to the housing 11, whereby the tip portion 43*t* once again resides within the needle shield 45. Every time a dose expelling action has been completed with the injection device 10 the above components have undergone the described respective movements. It is noted however, that in alternative embodiments of the invention the automatic return of components accomplished by means of the return spring 6 may be replaced with a manual return mechanism where e.g. a push button in the end wall 19 allows a user to manually press back said components after withdrawal of the tip portion 43*t* from the skin.

Figure 3:
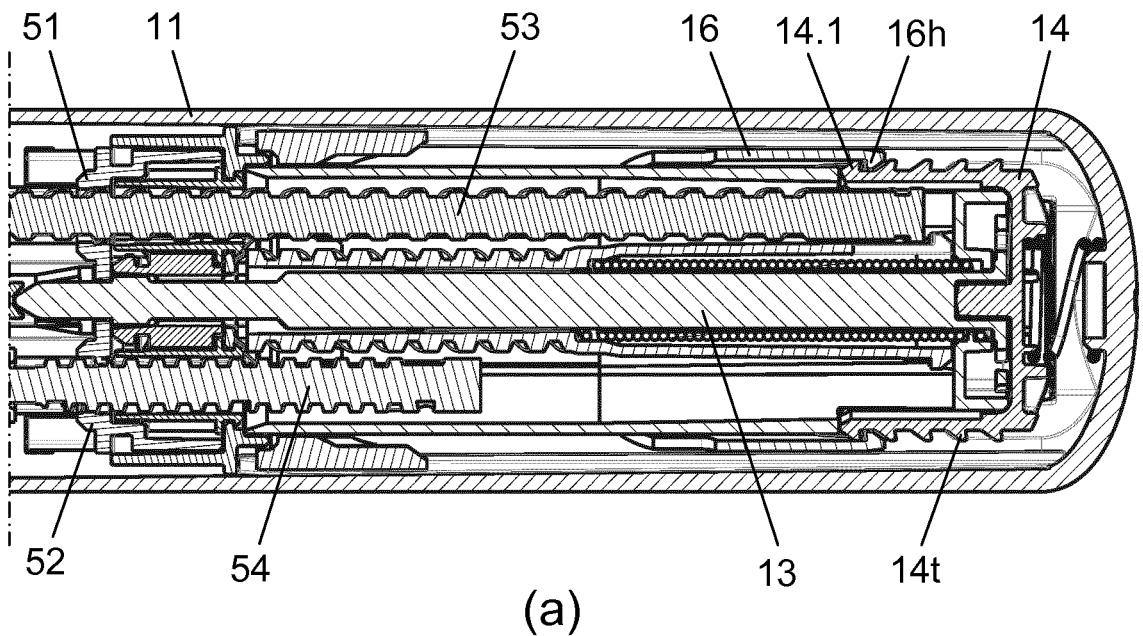
FIGS. 3(a)-(b) shows two different longitudinal section views of a proximal portion of the drug delivery device in an initial pre-use state.
Figure 3:
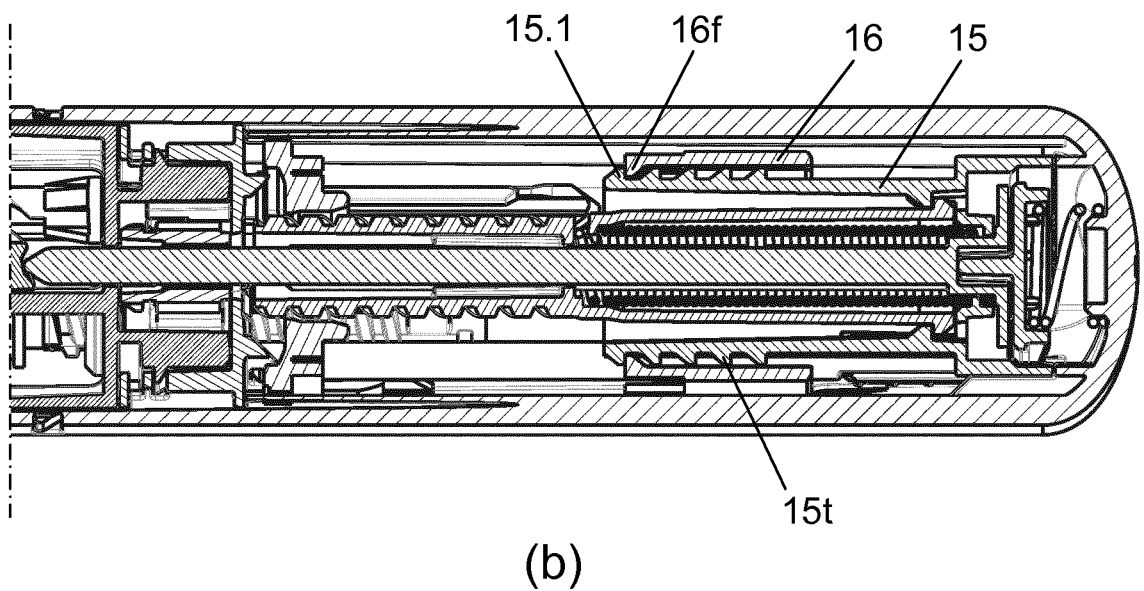

FIG. 3 depicts a proximal portion of the injection device 10 in two different longitudinal section views, where FIG. 3*a* notably shows the arrangement of the first piston rod 53 and the second piston rod 54 on either side of the rear activator 13, as well as an engagement between the return member 14 and the end-of-content ring 16. The first piston rod 53 is threadedly engaged with a first nut member 51, and the second piston rod 54, having a different pitch than the first piston rod 53, is threadedly engaged with a second nut member 52. FIG. 3*b* notably shows an engagement between the spring base 15 and the end-of-content ring 16.

In principle, the spring base 15 corresponds to the first component 1 in FIG. 1, the end-of-content ring 16 corresponds to the second component 2, and the return member 14 corresponds to the third component 3. Hence, the interactions between these three components during a dose expelling action provide for the dose counting mechanism of the injection device 10. The end-of-content ring 16 has a proximal arm with a hook 16*h* which initially engages a distal most tooth 14.1 of an axial return member toothing 14*t*, as seen in FIG. 3*a*, and a distal foot 16*f* which initially rests on a distal most tooth 15.1 of an axial spring base toothing 15*t*, as seen in FIG. 3*b*. The axial position of the return member 14 in FIG. 3 corresponds to the axial position in FIG. 2*a*, which, in combination with the axial position of the end-of-content ring 16 relative to the housing 11, means that the injection device 10 is in a state where an expelling of the very first dose has not yet commenced.

Figure 4:
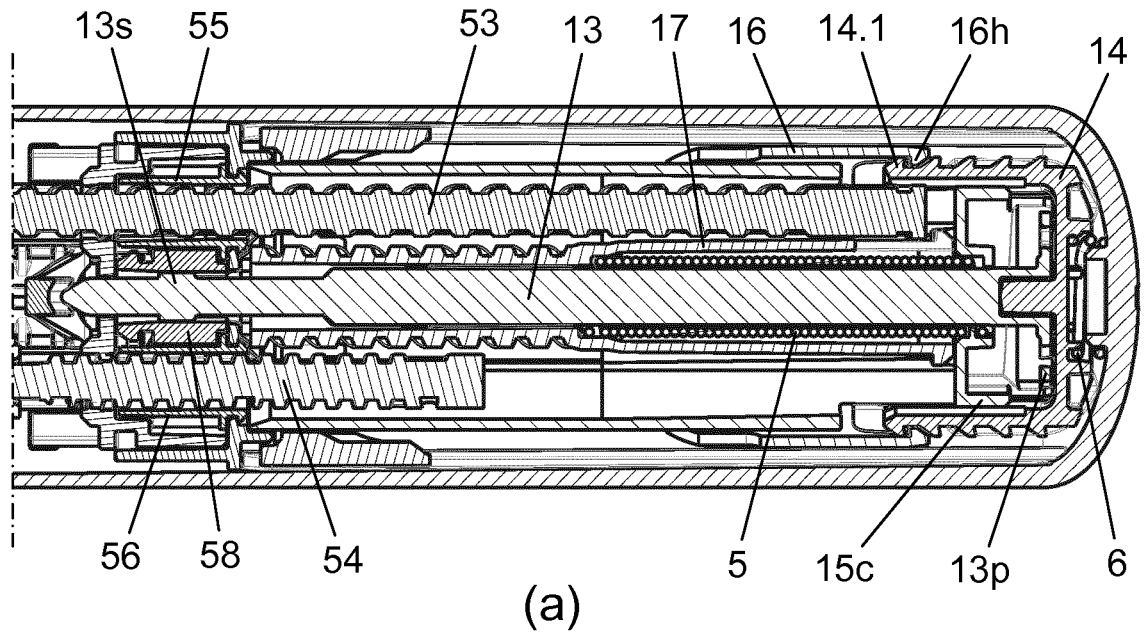
FIGS. 4(a)-(b) shows similar section views as in FIG. 3(a) at initiation of the first dose delivery from the drug delivery device.
Figure 4:
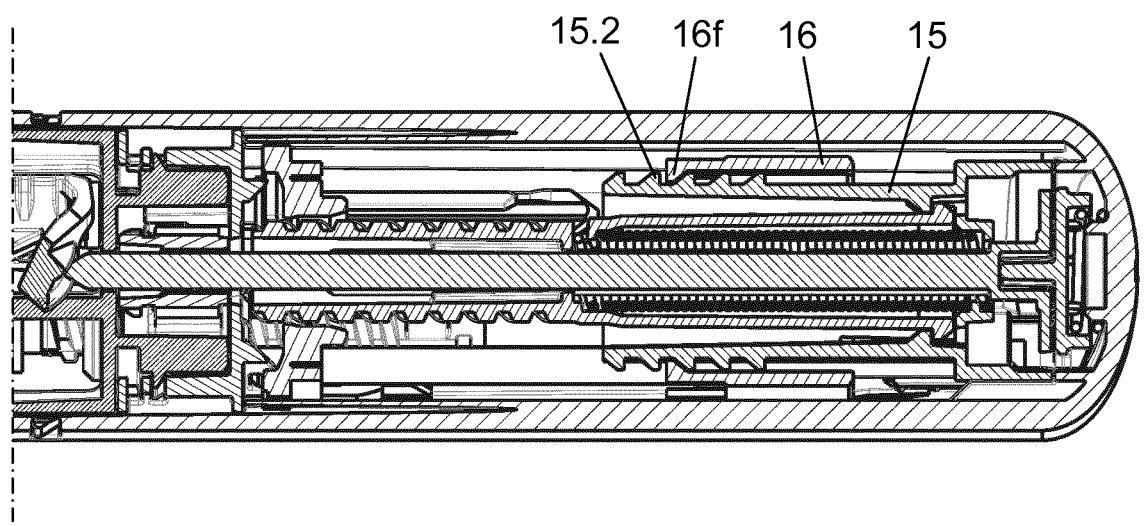
Figure 5:
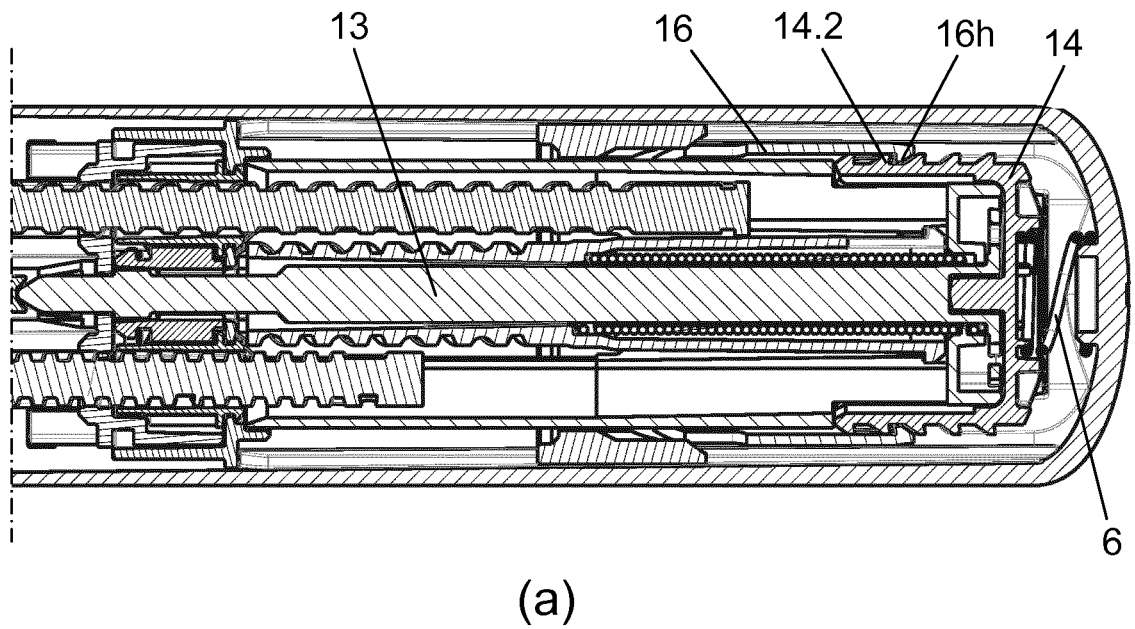
FIGS. 5(a)-(b) shows similar section views as in FIG. 3(a) following delivery of the first dose and removal of the drug delivery device from the skin.
Figure 5:
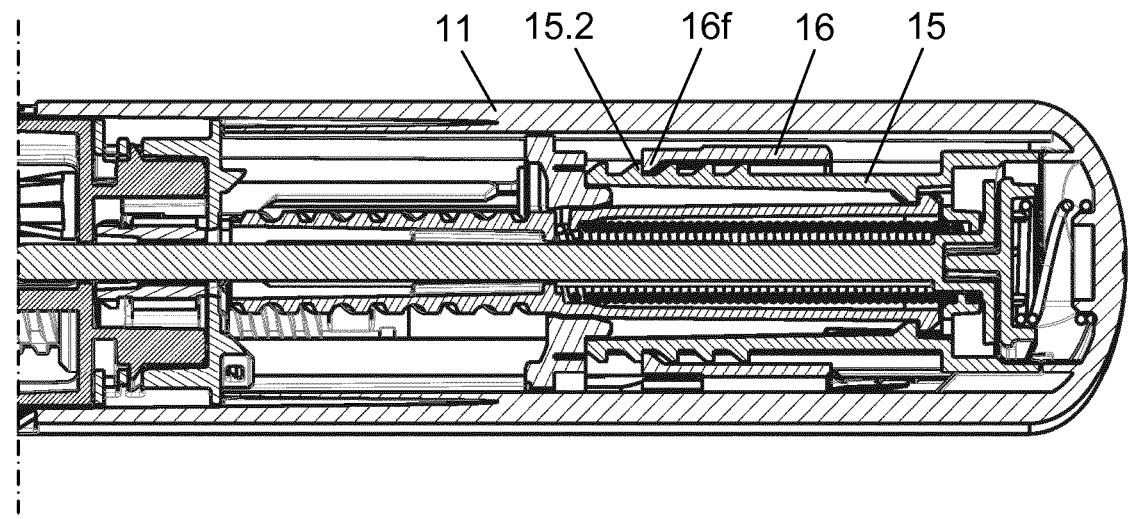
Figure 6:
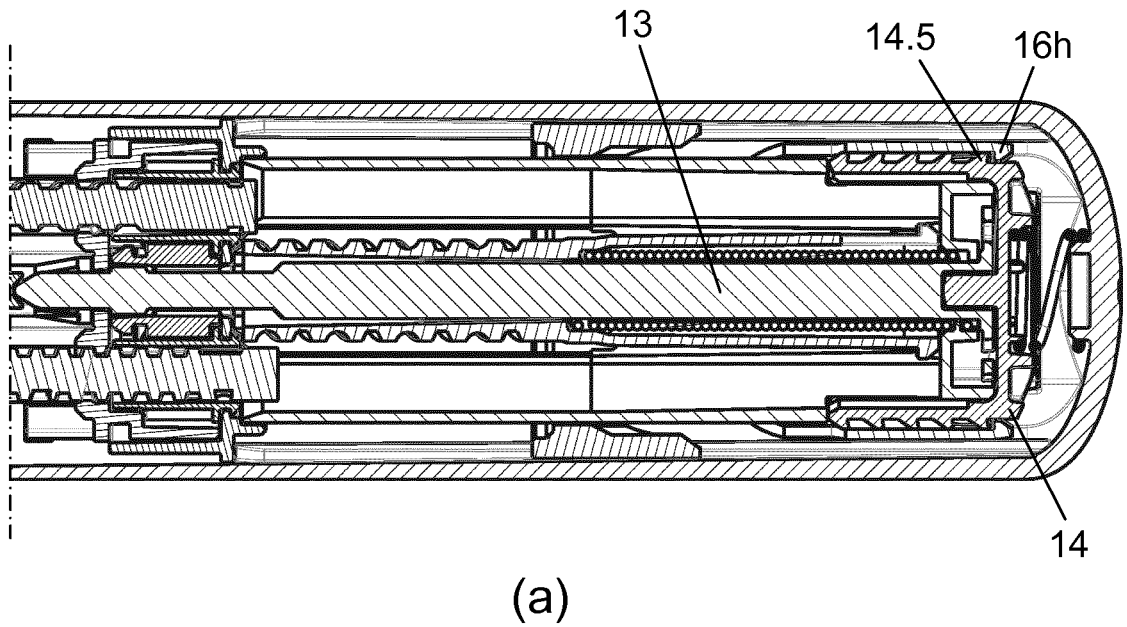
FIGS. 6(a)-(b) shows similar section views as in FIG. 3(a) following delivery of the last dose offered by the drug delivery device.
Figure 6:
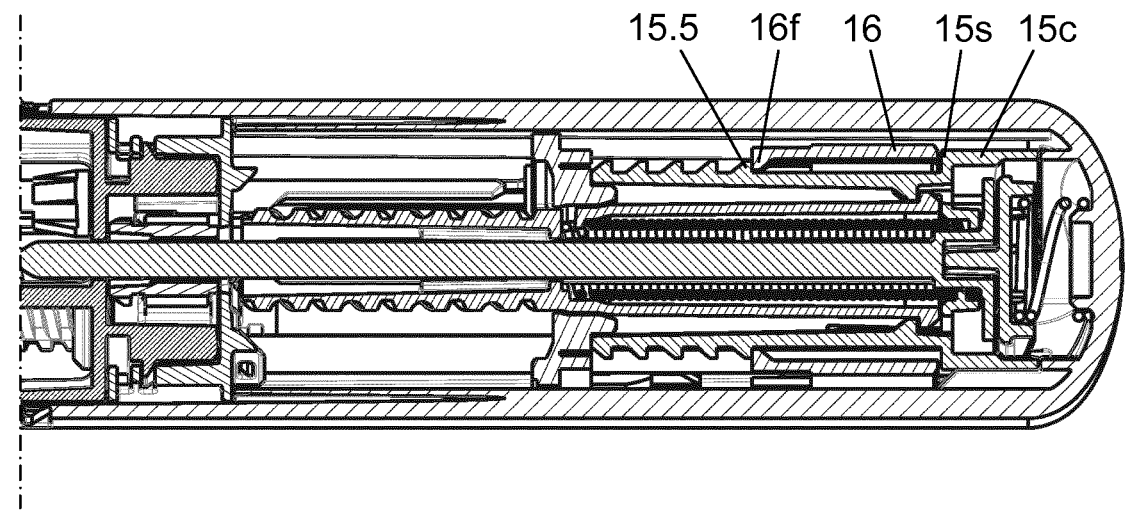

FIGS. 4-6 depict, through similar section views of the proximal portion, the injection device 10 in various subsequent states. FIG. 4 shows the injection device 10 in a state similar to that of FIG. 2*b*, where the tip portion 43*t* extends through the opening 46 and the injection mechanism is triggered. In particular, it is seen from FIG. 4a that the rear activator 13 has been displaced proximally, thus disengaging the pawls 13p from the spring base collar 15c. By this proximal displacement a spline section 13s of the rear activator 13 is slid into spline engagement with a central clutch 58. The central clutch 58 is rotationally coupled with a first piston rod driver 55 and a second piston rod driver 56 via respective cogwheel interfaces.

The first piston rod driver 55 is rotationally locked to the first piston rod 53, and the second piston rod driver 56 is rotationally locked to the second piston rod 54. Hence, when the rear activator 13 rotates as a consequence of the pawls 13p disengaging from the spring base collar 15c to release the drive spring 5 the central clutch 58 is forced to rotate along with the rear activator 13. This then causes a rotation of both the first piston rod driver 55 and the second piston rod driver 56, whereby the first piston rod 53 advances helically in the distal direction through the first nut member 51 and the second piston rod 54 advances helically in the distal direction through the second nut member 52.

The advancement of the first piston rod 53 results in an axial advancement of the piston in the first cartridge 35 and thereby in expelling of a first predetermined dose of the first substance through the front needle 43. Similarly, the advancement of the second piston rod 54 results in an axial advancement of the piston in the second cartridge and thereby in expelling of a second predetermined dose of the second substance through the front needle 43. The size of the first predetermined dose is determined by the total angular displacement of the spring clutch 17 during the relaxation of the drive spring 5 as well as the pitch of the first piston rod 53 and the size of the second predetermined dose is determined by the total angular displacement of the spring clutch 17 during the relaxation of the drive spring 5 as well as the pitch of the second piston rod 54. The total angular displacement of the spring clutch 17 during the relaxation of the drive spring 5 is the angular displacement exhibited by the spring clutch 17 as the loader nut 20n travels the non-self-locking thread 17t from the distal thread end to the proximal thread end.

Also, by the proximal displacement of the rear activator 13 the return member 14 has been urged towards the end wall 19, forcing the end-of-content ring 16 due to the engagement between the hook 16h and the distal most tooth 14.1. During the displacement of the end-of-content ring 16 the foot 16f has passed a second tooth 15.2 in the axial spring base toothing 15t, as shown in FIG. 4b, in a manner similar to what was described above in connection with FIG. 1b.

FIG. 5 shows the injection device 10 in a state where the return member 14 and the rear activator 13 have been returned to their initial axial positions in the housing 11 by the return spring 6 following a retraction of the tip portion 43t from the skin of the user. The distal motion of the return member 14 causes the hook 16h to pass a second tooth 14.2 in the axial return member toothing 14t, while the foot 16f rests against the second tooth 15.2 in the axial spring base toothing 15t. The first dose expelling action with the injection device 10 has thus lead to an incremental proximal displacement of the end-of-content ring 16 along the spring base 15 from the distal most tooth 15.1 to the second tooth 15.2 and relative to the return member 14 from the distal most tooth 14.1 to the second tooth 14.2.

At every dose expelling action the end-of-content ring 16 undergoes such incremental displacement relative to the spring base 15 and the return member 14, and the instant respective position of the foot 16f and the hook 16h can thus be used in a determination of the number of doses expelled and/or the number of doses still to be expelled from the injection device 10. For example, the spring base toothing 15t and/or the return member toothing 14t may be made visible through a window (not shown) in the housing 11.

The end-of-content ring 16 crawls up the spring base 15 from one tooth to the next, until the foot 16f rests on a proximal most tooth 15.5 in the axial spring base toothing 15t and the hook 16h engages a proximal most tooth 14.5 in the axial return member toothing 14t. This situation is depicted in FIG. 6, where FIG. 6a shows the position of the hook 16h and FIG. 6b shows the position of the foot 16f after retraction of the front needle 43 from the skin following a fourth dose expelling action with the injection device 10.

As can be seen from FIG. 6b in this state of the injection device 10 the end-of-content ring 16 is blocked from further proximal movement relative to the spring base 15 by a stop surface 15s on the spring base collar 15c. Any attempt to lift the rear activator 13 via proximal displacement of the front activator 12 will be unsuccessful as the return member 14 is prevented from proximal displacement relative to the housing 11 because of the engagement between the proximal most tooth 14.5 and the hook 16h. The needle shield 45 of a new (or the same) needle module 40 attached to the cartridge holder 30 can thus not be depressed to expose the tip portion 43t, this providing an end-of-content signal which indicates to the user that no further doses are available from the injection device 10.

As indicated above, when a dose expelling action is completed the loader nut 20n is positioned at the proximal thread end of the non-self-locking thread 17t. The protective cap 60 is adapted to be mounted on the cartridge holder 30 between dose expelling actions to protect the two cartridges. During the mounting onto the cartridge holder 30 the protective cap 60 reengages with the loader leg 20l, such that when the protective cap 60 is subsequently dismounted from the cartridge holder 30 in order to prepare for a next dose expelling action the loader nut 20n will be forced to travel the non-self-locking thread 17t to the distal thread end, thereby straining the drive spring 5 by the resulting rotation of the spring clutch 17.

Figure 7:
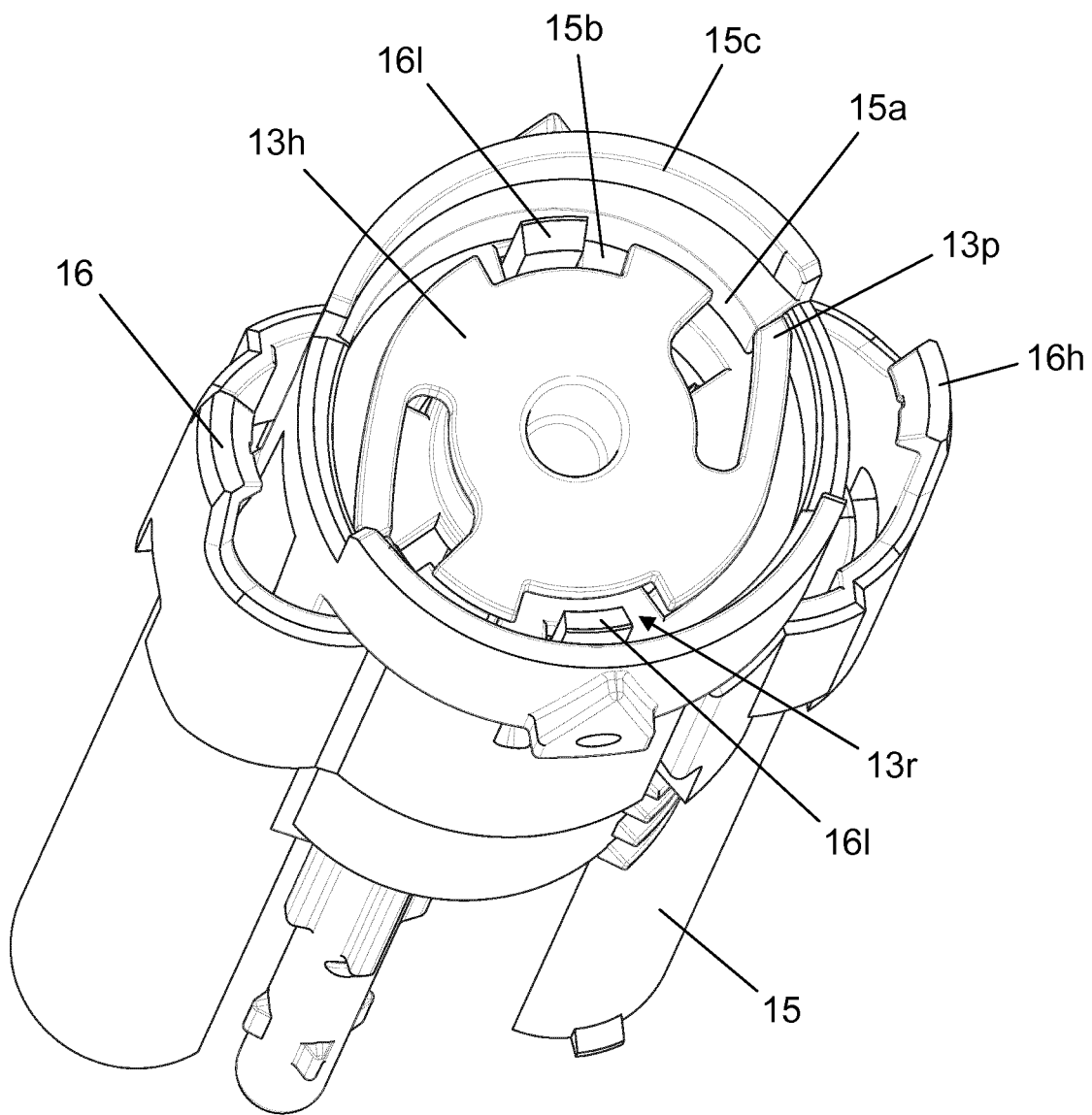

An additional end-of-content indication is provided in the injection device 10 which already at dismounting of the protective cap 60 signals to the user that a new device is needed. FIG. 7 is a perspective top view of selected components in the housing 11, showing their respective relative positions following the last possible dose expelling. The view reveals a transversal collar bottom 15b of the spring base collar 15c as well as a pair of interior arcs 15a of varying thickness constituting a support for the pawls 13p that restricts counter-clockwise rotation of the rear activator 13 relative to the spring base 15. The pawls 13p form part of an activator head 13h which is a radially enlarged end portion of the rear activator 13.

The end-of-content ring 16 comprises a pair of proximally extending lock arms 16l, each of which passes through a dedicated bore in the collar bottom 15b and into a recess 13r in the periphery of the activator head 13h during the incremental movement of the foot 16f to the proximal most tooth 15.5 in the axial spring base toothing 15t. This effectively restricts also clockwise rotation of the rear activator 13 relative to the spring base 15, and as a consequence the spring clutch 17 will be rotationally locked with respect to the housing 11. Since the spring clutch 17 is unable to rotate the loader nut 20n will be unable to travel the non-self-locking thread 17t, which means that the loader leg 20l will be axially locked relative to the housing 11. Accordingly, when the user tries to pull off the protective cap 60 the loader 20 will provide resistance to the axial dismounting motion.

Depending on the exact construction of the snap interface 20s the protective cap 60 will either be stuck on the cartridge holder 30, or a part of the cap/loader interface will flex to allow disengagement of the protective cap 60 from the loader leg 20l when the axial separating force between the protective cap 60 and the housing 11 is sufficiently large. In any case the user will experience a significantly greater resistance to the dismounting of the protective cap 60 than previously.

Hence, if the user is one who normally changes the needle module 40 after each dose expelling, as recommended, (s)he can spare the attachment of a new needle module, as the impeded dismounting of the protective cap 60 provides a signal of an end-of-content state of the injection device 10 such that a check for needle shield blockage will not be needed.

FIG. 8 is a perspective view of the drug delivery device 10 in a state where the protective cap 60 is dismounted from the cartridge holder 30. A protrusion 31 is provided on either side of the cartridge holder 30 for reception and releasable retention of the needle module 40 and an orifice 32 provides for access of the activator arm 44 to the interior of the cartridge holder 30 for the operative connection with the front activator 12 described above.

The invention claimed is:

1. A drug delivery device for executing a predetermined number of dose expelling actions, the drug delivery device comprising:
    a housing extending along an axis and accommodating a dose expelling mechanism,
    a reciprocating element operatively coupled with the dose expelling mechanism and configured to undergo a predefined motion relative to the housing during each dose expelling action to allow a dose to be expelled, the predefined motion comprising displacement in a first axial direction from a first position to a second position followed by displacement in a second axial direction from the second position to the first position,
    a counter element being movable in the first axial direction relative to the housing, a first unidirectional ratchet mechanism configured to prevent motion in the first axial direction and allow motion in the second axial direction of the reciprocating element relative to the counter element, and
    a second unidirectional ratchet mechanism configured to allow motion in the first axial direction and prevent motion in the second axial direction of the counter element relative to the housing.

2. The drug delivery device according to claim 1, further comprising a base member being axially and rotationally fixed with respect to the housing, wherein the first unidirectional ratchet mechanism comprises a first axial toothing on one of the reciprocating element and the counter element and a pawl member on the other of the reciprocating element and the counter element, and the second unidirectional ratchet mechanism comprises a second axial toothing on one of the counter element and the base member and a pawl member on the other of the counter element and the base member.

3. The drug delivery device according to claim 1, wherein the counter element is configured to undergo motion in the first axial direction relative to the housing from a pre-use position to an end-of-content position in a number of steps which correspond to the predetermined number of dose expelling actions and to enter into axial interlocking engagement with the base member in response to reaching the end-of-content position, thereby becoming prevented from further motion in the first axial direction relative to the housing.

4. The drug delivery device according to claim 1, further comprising a drug reservoir holder arranged in an axial extension of the housing, wherein the dose expelling mechanism comprises an activation structure being operable from a distal end portion of the drug reservoir holder to displace the reciprocating element in the first axial direction against a biasing force.

5. The drug delivery device according to claim 4, wherein the drug reservoir holder comprises reception structure configured to receive a needle module at the distal end portion and to provide for operative coupling of an axially movable portion of the needle module with the activation structure.

6. The drug delivery device according to claim 5, wherein the reception structure comprises a received needle module, and wherein the axially movable portion of the needle module is a needle shield adapted to selectively cover and uncover a skin insertable front needle, and wherein the needle shield of the received needle module is configured to displace the reciprocating element in the first axial direction in response to an uncovering of the skin insertable front needle.

7. The drug delivery device according to claim 4, further comprising a dose preparing structure configured to prepare a dose to be delivered from the drug delivery device in response to distal motion of a loading member relative to the housing, and a protective cap for the drug reservoir holder, the protective cap being operatively coupled with the dose preparing structure when covering the drug reservoir holder and configured to move the loading member distally relative to the housing in response to being dismounted from the cartridge holder.

8. The drug delivery device according to claim 7, wherein the dose expelling mechanism is powered by a torsion spring member, wherein the dose preparing structure comprises a spring straining mechanism for straining the torsion spring member and is configured to convert distal motion of the loading member relative to the housing to rotation of a spring straining member relative to the housing, and wherein the counter element is rotationally fixed with respect to the housing and configured to enter into rotational interlocking engagement with the spring straining member in response to reaching the end-of-content position, thereby preventing distal motion of the loading member relative to the housing.

* * * * *